(12) United States Patent
Uchiyama et al.

(10) Patent No.: US 7,960,327 B2
(45) Date of Patent: Jun. 14, 2011

(54) CLEANSING COMPOSITION

(75) Inventors: Tomoko Uchiyama, Wakayama (JP); Hayato Yoshikawa, Wakayama (JP)

(73) Assignee: Kao Corporation, Tokyo (JP)

( * ) Notice: Subject to any disclaimer, the term of this patent is extended or adjusted under 35 U.S.C. 154(b) by 187 days.

(21) Appl. No.: 12/306,006

(22) PCT Filed: Jul. 2, 2007

(86) PCT No.: PCT/JP2007/000724
§ 371 (c)(1),
(2), (4) Date: Dec. 22, 2008

(87) PCT Pub. No.: WO2008/004342
PCT Pub. Date: Jan. 10, 2008

(65) Prior Publication Data
US 2009/0253603 A1 Oct. 8, 2009

(30) Foreign Application Priority Data

Jul. 4, 2006 (JP) ................................. 2006-184830

(51) Int. Cl.
*A61K 7/50* (2006.01)
(52) U.S. Cl. ........ 510/130; 510/136; 510/156; 510/424; 510/505; 510/506; 424/70.1
(58) Field of Classification Search ........................ None
See application file for complete search history.

(56) References Cited

U.S. PATENT DOCUMENTS

| | | | |
|---|---|---|---|
| 3,959,160 A | 5/1976 | Horsler et al. | |
| 2003/0170197 A1 | 9/2003 | Terazaki et al. | |
| 2004/0156815 A1 | 8/2004 | Sakai et al. | |
| 2006/0160714 A1 * | 7/2006 | Terada ........................ | 510/119 |

FOREIGN PATENT DOCUMENTS

| | | |
|---|---|---|
| EP | 0 627 216 A2 | 12/1994 |
| EP | 0 627 216 A3 | 12/1994 |
| EP | 1 428 499 A2 | 6/2004 |
| EP | 1 428 499 A3 | 6/2004 |
| EP | 1 676 567 A1 | 7/2006 |
| EP | 1676566 A1 | 7/2006 |
| JP | 2003-212733 | 7/2003 |
| JP | 2003 212733 | 7/2003 |
| JP | 2004 75546 | 3/2004 |
| JP | 2004-91522 | 3/2004 |
| JP | 2004-155723 | 6/2004 |
| JP | 2004-168951 | 6/2004 |
| JP | 2004 168951 | 6/2004 |
| JP | 2004 203785 | 7/2004 |
| JP | 2005 350446 | 12/2005 |
| JP | 2006 182728 | 7/2006 |
| JP | 2006 282613 | 10/2006 |

OTHER PUBLICATIONS

U.S. Appl. No. 12/307,382, filed Jan. 5, 2009, Uchiyama, et al.
Extended European Search Report issued Sep. 23, 2010 in PCT/JP2007/000724.

* cited by examiner

*Primary Examiner* — Necholus Ogden, Jr.
(74) *Attorney, Agent, or Firm* — Oblon, Spivak, McClelland, Maier & Neustadt, L.L.P.

(57) ABSTRACT

Provided is a detergent composition containing a polyoxyethylene alkyl ether sulfate or an alkyl sulfate which composition is excellent and creamy in foam quality, and excellent in storage stability. The detergent composition contains the following components (A), (B) and (C):

(A) a polyoxyethylene alkyl ether sulfate or an alkyl sulfate represented by a general formula (1):

$$R^1O(CH_2CH_2O)_nSO_3M \quad (1);$$

(B) myristyl alcohol;
(C) one or more nonionic surfactants selected from the group consisting of an alkoxylate (C-1) represented by a general formula (2) and a glyceryl ether (C-2) represented by a general formula (3):

$$R^2O\text{-}(AO)_n\text{—}R^3 \quad (2)$$

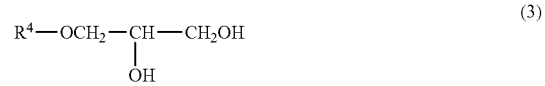

wherein the weight ratio of the component (A) to the component (B) is (A)/(B)=91.5/8.5 to 80/20, the weight ratio of the component (A) to the component (C) is (A)/(C)=98/2 to 85/15, the weight ratio of the component (B) to the component (C) is (B)/(C)=90/10 to 30/70, and the content of the component (B) is 1.6 to 14% by weight.

12 Claims, No Drawings

CLEANSING COMPOSITION

FIELD OF THE INVENTION

The present invention relates to a detergent composition containing a polyoxyethylene alkyl ether sulfate or an alkyl sulfate, which is improved in foam quality and is excellent in stability.

BACKGROUND OF THE INVENTION

In detergent compositions, various surfactants are used according to the application purposes thereof, and many of such detergent compositions have a foam quality rough and lacking elasticity. Widely used detergent compositions containing polyoxyethylene alkyl ether sulfates or alkyl sulfates are excellent detergent compositions in the sense that such detergent compositions are excellent in foaming and are hardly affected by water quality; however, such detergent compositions are inferior in foam quality to detergent compositions including soaps as the fundamental ingredients thereof to bring about elastic and creamy foams having fine particle sizes. If such foam qualities, rough and lacking elasticity, of polyoxyethylene alkyl ether sulfates or alkyl sulfates can be improved into creamy foam qualities and detergent compositions excellent in storage stability can thereby be obtained, various formulations can be designed, and such formulations as detergent compositions are useful as body detergents for the skin or hair preferring creamy foam quality.

In Patent Document 1, it is disclosed that a liquid detergent containing micellar-growth-promoting agents such as a non-soap anionic surfactant, an amphoteric surfactant, a nonionic surfactant having an HLB of 6 to 18 and a higher alcohol is excellent in detergency and satisfactory in low-temperature stability. In Patent Document 2, it is disclosed that a hair detergent containing a sulfate residue-containing anionic surfactant, a higher alcohol having 10 to 14 carbon atoms and a cationic polymer has a foam quality satisfactory in foaming and slippability at the time of cleansing the hair, has a smooth feeling at the time of rinsing the hair, and is excellent in feeling of use. In Patent Document 3, it is disclosed that a detergent composition including an anionic surfactant, a specific nonionic surfactant and water and taking a gel or liquid crystalline form is highly viscous, satisfactory in resistance to sagging at the time of dealing with hand or a tool and nevertheless satisfactory in spreading performance, high in storage stability, and quick and satisfactory in foaming. In Patent Document 4, it is disclosed that a hair detergent including a sulfate surfactant, an alkyl glyceryl ether, silicone oil, a cationic polymer and myristyl alcohol brings about a foam quality satisfactory in foaming and slippability, smooth feeling at the time of rinsing, and gloss and well-shapedness to the finished hair, and is satisfactory in low-temperature stability and weakly irritant.

However, none of these detergent compositions simultaneously satisfies the foam quality improvement and the storage stability. In the detergent composition including a polyoxyethylene alkyl ether sulfate or an alkyl sulfate, a technique is adopted in which a higher alcohol is added for the purpose of attaining creamy foam quality; however, the storage stability of this composition is not sufficiently satisfactory. Additionally, the conditioning shampoo in Example 9 of Patent Document 4 cannot bring about creamy foam.

Patent Document 1: JP-A-2004-91522
Patent Document 2: JP-A-2003-212733
Patent Document 3: JP-A-2004-168951
Patent Document 4: EP 1676566 A

SUMMARY OF THE INVENTION

The present invention provides a detergent composition containing the following components (A), (B) and (C):

(A) a polyoxyethylene alkyl ether sulfate or an alkyl sulfate represented by a general formula (1):

$$R^1O(CH_2CH_2O)_nSO_3M \qquad (1)$$

wherein $R^1$ represents a straight chain or branched chain, alkyl or alkenyl group having 8 to 18 carbon atoms, an average addition number of moles n represents a number of 0 to 5, and M represents an alkali metal atom, an alkanolamine or ammonium;

(B) myristyl alcohol;

(C) one or more nonionic surfactants selected from the group consisting of an alkoxylate (C-1) represented by a general formula (2) and a glyceryl ether (C-2) represented by a general formula (3), (C-1) an alkoxylate represented by the general formula (2):

$$R^2O-(AO)_n-R^3 \qquad (2)$$

wherein $R^2$ represents a straight chain or branched chain, alkyl or alkenyl group having 8 to 10 carbon atoms, AO represents an alkyleneoxy group having 2 to 4 carbon atoms, an average addition number of moles n represents a number of 0.5 or more and less than 4.0, and $R^3$ represents a hydrogen atom or a methyl group; and (C-2) a glyceryl ether represented by the general formula (3):

$$R^4-OCH_2-\underset{\underset{OH}{|}}{CH}-CH_2OH \qquad (3)$$

wherein $R^4$ represents a straight chain or branched chain, alkyl or alkenyl group having 6 to 14 carbon atoms, wherein the weight ratio of the component (A) to the component (B) is (A)/(B)=91.5/8.5 to 80/20, the weight ratio of the component (A) to the component (C) is (A)/(C)=98/2 to 85/15, the weight ratio of the component (B) to the component (C) is (B)/(C)=90/10 to 30/70, and the content of the component (B) is 1.6 to 14% by weight.

Additionally, the present invention provides a method for producing a detergent composition containing the following components (A), (B) and (C):

(A) a polyoxyethylene alkyl ether sulfate or an alkyl sulfate represented by the general formula (1):

$$R^1O(CH_2CH_2O)_nSO_3M \qquad (1)$$

wherein $R^1$ represents a straight chain or branched chain, alkyl or alkenyl group having 8 to 18 carbon atoms, the average addition number of moles n represents a number of 0 to 5, and M represents an alkali metal atom, an alkanolamine or ammonium;

(B) myristyl alcohol;

(C) one or more nonionic surfactants selected from the group consisting of an alkoxylate (C-1) represented by the general formula (2) and a glyceryl ether (C-2) represented by the general formula (3), (C-1) an alkoxylate represented by the general formula (2):

$$R^2O-(AO)_n-R^3 \qquad (2)$$

wherein $R^2$ represents a straight chain or branched chain, alkyl or alkenyl group having 8 to 10 carbon atoms, AO represents an alkyleneoxy group having 2 to 4 carbon atoms, the average addition number of moles n represents a number of 0.5 or more and less than 4.0, and $R^3$ represents a hydrogen atom or a methyl group; and (C-2) a glyceryl ether represented by the general formula (3):

wherein $R^4$ represents a straight chain or branched chain, alkyl or alkenyl group having 6 to 14 carbon atoms, wherein the following components (A), (B) and (C) are mixed together in such a way that the weight ratio of the component (A) to the component (B) is (A)/(B)=91.5/8.5 to 80/20, the weight ratio of the component (A) to the component (C) is (A)/(C)=98/2 to 85/15, the weight ratio of the component (B) to the component (C) is (B)/(C)=90/10 to 30/70, and the content of the component (B) is 1.6 to 14% by weight.

Further, the present invention provides a method for cleansing the skin by using a composition containing the following components (A), (B) and (C):

(A) a polyoxyethylene alkyl ether sulfate or an alkyl sulfate represented by the general formula (1):

$$R^1O(CH_2CH_2O)_nSO_3M \quad (1)$$

wherein $R^1$ represents a straight chain or branched chain, alkyl or alkenyl group having 8 to 18 carbon atoms, the average addition number of moles n represents a number of 0 to 5, and M represents an alkali metal atom, an alkanolamine or ammonium;

(B) myristyl alcohol;

(C) one or more nonionic surfactants selected from the group consisting of an alkoxylate (C-1) represented by the general formula (2) and a glyceryl ether (C-2) represented by the general formula (3), (C-1) an alkoxylate represented by the general formula (2):

wherein $R^2$ represents a straight chain or branched chain, alkyl or alkenyl group having 8 to 10 carbon atoms, AO represents an alkyleneoxy group having 2 to 4 carbon atoms, the average addition number of moles n represents a number of 0.5 or more and less than 4.0, and $R^3$ represents a hydrogen atom or a methyl group; and (C-2) a glyceryl ether represented by the general formula (3):

wherein $R^4$ represents a straight chain or branched chain, alkyl or alkenyl group having 6 to 14 carbon atoms, wherein the weight ratio of the component (A) to the component (B) is (A)/(B)=91.5/8.5 to 80/20, the weight ratio of the component (A) to the component (C) is (A)/(C)=98/2 to 85/15, the weight ratio of the component (B) to the component (C) is (B)/(C)=90/10 to 30/70, and the content of the component (B) is 1.6 to 14% by weight.

Further, the present invention provides use of a composition as a skin detergent, the composition containing the following components (A), (B) and (C):

(A) a polyoxyethylene alkyl ether sulfate or an alkyl sulfate represented by the general formula (1):

$$R^1O(CH_2CH_2O)_nSO_3M \quad (1)$$

wherein $R^1$ represents a straight chain or branched chain, alkyl or alkenyl group having 8 to 18 carbon atoms, the average addition number of moles n represents a number of 0 to 5, and M represents an alkali metal atom, an alkanolamine or ammonium;

(B) myristyl alcohol;

(C) one or more nonionic surfactants selected from the group consisting of an alkoxylate (C-1) represented by the general formula (2) and a glyceryl ether (C-2) represented by the general formula (3), (C-1) an alkoxylate represented by the general formula (2):

wherein $R^2$ represents a straight chain or branched chain, alkyl or alkenyl group having 8 to 10 carbon atoms, AO represents an alkyleneoxy group having 2 to 4 carbon atoms, the average addition number of moles n represents a number of 0.5 or more and less than 4.0, and $R^3$ represents a hydrogen atom or a methyl group; and (C-2) a glyceryl ether represented by the general formula (3):

wherein $R^4$ represents a straight chain or branched chain, alkyl or alkenyl group having 6 to 14 carbon atoms, wherein the weight ratio of the component (A) to the component (B) is (A)/(B)=91.5/8.5 to 80/20, the weight ratio of the component (A) to the component (C) is (A)/(C)=98/2 to 85/15, the weight ratio of the component (B) to the component (C) is (B)/(C)=90/10 to 30/70, and the content of the component (B) is 1.6 to 14% by weight.

DETAILED DESCRIPTION OF THE INVENTION

An objective of the present invention is to provide a detergent composition containing a polyoxyethylene alkyl ether sulfate or an alkyl sulfate, the detergent composition being excellent in foam amount, creamy in foam quality and excellent in storage stability.

The present inventors have found that by combining a polyoxyethylene alkyl ether sulfate or an alkyl sulfate with myristyl alcohol among higher alcohols and a nonionic surfactant having a specific structure, and further, by mixing these in a specific ratio, there can be obtained a detergent composition excellent in foam amount, creamy in foam quality and excellent in storage stability.

The detergent composition of the present invention containing a polyoxyethylene alkyl ether sulfate or an alkyl sulfate is excellent in foam amount, creamy in foam quality and excellent in storage stability. Consequently, the detergent composition of the present invention is useful as a skin or hair detergent, and further as a skin detergent.

Hereinafter, the present invention is described in more detail.

In the polyoxyethylene alkyl ether sulfate or the alkyl sulfate as the component (A), used in the present invention, represented by the above general formula (1), $R^1$ is a straight chain or branched chain, alkyl or alkenyl group having 8 to 18 carbon atoms; such a group preferably has 10 to 16 carbon atoms, more preferably 12 to 14 carbon atoms from the viewpoint of the detergency and foamability, and is preferably an alkyl group. Additionally, the alkyl group or the alkenyl group as $R^1$ may be of a straight chain or a branched chain, and is preferably of a straight chain. The average addition number of moles n represents a number of 0 to 5, and is preferably 1 to 3, more preferably 1 to 2 from the viewpoint of the detergency and foamability. M represents an alkali metal atom, an alkanolamine or ammonium; examples of the alkali metal include sodium and potassium, and preferable of these is sodium. Preferable as the alkanolamine is triethanolamine.

Specific examples of the component (A) preferably include sodium polyoxyethylene(2)lauryl ether sulfate and ammonium polyoxyethylene(1)lauryl ether sulfate, and more preferably sodium polyoxyethylene(2)lauryl ether sulfate.

The content of the component (A) is preferably 5 to 70% by weight, more preferably 10 to 70% by weight and even more preferably 12 to 65% by weight in the detergent composition of the present invention from the viewpoint of the foamability. When the detergent composition of the present invention is a composition such as a face wash, the content of the component (A) is preferably 30 to 70% by weight, more preferably 30 to 65% by weight and even more preferably 30 to 60% by weight in the detergent composition. Additionally, when the detergent composition of the present invention is a composition such as a liquid body detergent, the content of the component (A) is preferably 5 to 25% by weight, more preferably 5 to 20% by weight and even more preferably 10 to 20% by weight in the detergent composition.

The component (B) used in the present invention is myristyl alcohol. According to the investigation of the present inventors, when the component (B) is combined with the component (A), among various higher alcohols, myristyl alcohol is particularly excellent in the effect of generating foam small in foam particle size, high in viscoelasticity and creamy. Specifically, the foam particle size is smaller when the component (A) is combined with myristyl alcohol than when combined with lauryl alcohol or palmityl alcohol, and the foam is creamy when combined with myristyl alcohol. Additionally, the viscoelasticity of the foam obtained when the component (A) is combined with myristyl alcohol is higher than that obtained when the component (A) is combined with lauryl alcohol or palmityl alcohol, and the foam is elastic when the component (A) is combined with myristyl alcohol.

The content of myristyl alcohol (B) is 1.6 to 14% by weight, preferably 1.6 to 10% by weight in the detergent composition of the present invention for the purpose of obtaining an appropriate foam amount and creamy foam quality. When the composition of the present invention is a composition such as a face wash, the content of the component (B) is preferably 2 to 14% by weight, more preferably 4 to 14% by weight and even more preferably 4 to 10% by weight in the detergent composition. Additionally, when the detergent composition of the present invention is a composition such as a liquid body detergent, the content of the component (B) is preferably 1.6 to 3% by weight, and more preferably 1.6 to 2.5% by weight in the detergent composition.

The component (C) includes one or more nonionic surfactants selected from the group consisting of the alkoxylate (C-1) and the glyceryl ether (C-2). Here, in the general formula (2) representing the alkoxylate (C-1), $R^2$ is a straight chain or branched chain, alkyl or alkenyl group having 8 to 10 carbon atoms. From the viewpoint of reducing the odor, a straight chain alkyl group is preferable. From the viewpoint of the foamability, $R^2$ preferably has 8 carbon atoms; when two or more alkyl groups are mixed, the proportion of the alkyl group having 8 carbon atoms is preferably 50% or more, more preferably 80% or more and even more preferably 98% or more.

In the general formula (2), AO is an alkyleneoxy group having 2 to 4 carbon atoms; a propyleneoxy group (hereinafter referred to as PO) and/or an ethyleneoxy group (hereinafter referred to as EO) is preferable; POs and EOs may be arranged in blocks or randomly, and are preferably arranged in blocks; from the viewpoint of reducing the odor, POs and EOs are preferably arranged in blocks in the order of PO and EO; and more preferably, only POs are arranged in blocks.

In the compound represented by the general formula (2), the average addition number of moles n represents a number of 0.5 or more and less than 4.0, and is preferably 1.0 to 3.0, more preferably 2.0 to 3.0, and even more preferably 2.0 to 2.5, from the viewpoint of the foamability.

$R^3$ in the general formula (2) represents a hydrogen atom or a methyl group, and is preferably a hydrogen atom.

In the general formula (3) representing glyceryl ether (C-2), $R^4$ represents a straight chain or branched chain, alkyl or alkenyl group having 6 to 14 carbon atoms; $R^4$ is preferably, for example, an alkyl group having 4 to 12 carbon atoms such as a n-hexyl group, an isohexyl group, a n-heptyl group, a n-octyl group, a 2-ethylhexyl group, a n-nonyl group, a n-decyl group, an isodecyl group or a n-lauryl group, more preferably an alkyl group having 6 to 11 carbon atoms, even more preferably an alkyl group having 6 to 10 carbon atoms, and preferably an alkyl group having 8 to 10 carbon atoms among others (more preferably a 2-ethylhexyl group or an isodecyl group).

Preferable in the component (C-2) is, from the viewpoint of the foam quality improvement or the storage stability, 2-ethylhexyl glyceryl ether or isodecyl glyceryl ether, and more preferably 2-ethylhexyl glyceryl ether.

For the purpose of attaining the storage stability of the detergent composition, in particular, preventing the two-layer separation of the detergent at the time of storage, the component (C) is contained in the detergent composition of the present invention preferably in a content of 0.05 to 14% by weight, more preferably 0.1 to 12% by weight, and even more preferably 0.5 to 12% by weight. When the detergent composition of the present invention is a composition such as a face wash, the content of the component (C) is preferably 2 to 14% by weight, more preferably 2 to 12% by weight and even more preferably 4 to 12% by weight in the detergent composition. Additionally, when the detergent composition of the present invention is a composition such as a liquid body detergent, the content of the component (C) is preferably 0.05 to 3% by weight, more preferably 0.1 to 2.5% by weight and even more preferably 0.5 to 2.5% by weight in the detergent composition.

In the detergent composition of the present invention, the mixing ratios (weight ratios) between the components (A), (B) and (C) are extremely important for the purpose of attaining the compatibility between the foam quality improvement and the storage stability. Specifically, for the purpose of ensuring the foam quality improvement effect and the storage stability, the mixing ratios between the components (A), (B)

and (C) are as follows: (A)/(B)=91.5/8.5 to 80/20, (A)/(C)=98/2 to 85/15 and (B)/(C)=90/10 to 30/70. Within these ranges, (A)/(B) preferably ranges from 91.5/8.5 to 82/18, and more preferably from 91.5/8.5 to 85/15; (A)/(C) preferably ranges from 98/2 to 88/12, and more preferably from 97.5/2.5 to 88/12; and (B)/(C) preferably ranges from 90/10 to 40/60, and more preferably 85/15 to 40/60.

By further mixing a cationic polymer (D) in the detergent composition of the present invention, the foam viscosity can be improved and the foam quality can be further improved. Examples of the cationic polymer include one or more selected from the group consisting of the following (a) to (d):

(a) a cationic group-containing copolymer obtained by a radical polymerization including as essential constituent monomers at least one nonionic group-containing vinyl monomer represented by a general formula (I) or (II), at least one cationic group-containing vinyl monomer represented by a general formula (III) or (IV), and at least one crosslinkable vinyl monomer having in the molecule thereof at least two groups selected from a vinyl group, an acryloyl group, a methacryloyl group and an allyl group:

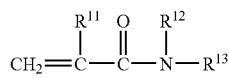

(I)

wherein $R^{11}$ represents a hydrogen atom or a methyl group, and $R^{12}$ and $R^{13}$ are the same or different and each represent a hydrogen atom or a straight chain or branched chain, alkyl or alkenyl group having 1 to 4 carbon atoms,

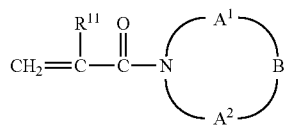

(II)

wherein $R^{11}$ represents the same meaning as above, $A^1$ and $A^2$ are the same or different and each represent a group represented by a formula —$(CH_2)_m$— with the proviso that m represents an integer of 2 to 6, and B represents a group —O— or —$CH_2$—,

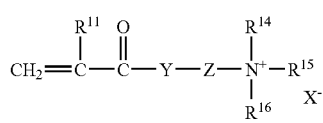

(III)

wherein $R^{11}$ represents the same meaning as above, $R^{14}$ and $R^{15}$ are the same or different and each represent an alkyl or alkenyl group having 1 to 4 carbon atoms, $R^{16}$ represents a hydrogen atom or an alkyl group having 1 to 4 carbon atoms, Y represents a group —O—, —NH—, —$CH_2$— or —O—$CH_2CH(OH)$—, Z represents a straight chain or branched chain alkylene group having 1 to 4 carbon atoms with the proviso that this group has 0 to 3 carbon atoms when Y is —$CH_2$—, and $X^-$ represents a conjugate base of an acid, a halide ion or an alkyl sulfate group having 1 to 4 carbon atoms,

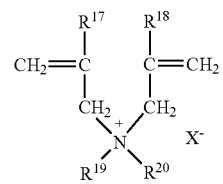

(IV)

wherein $R^{17}$ and $R^{18}$ are the same or different and each represent a hydrogen atom or a methyl group, $R^{19}$ and $R^{20}$ are the same or different and each represent a hydrogen atom or an alkyl group having 1 to 4 carbon atoms, and $X^-$ represents the same meaning as above;

(b) a cationized cellulose derivative;

(c) a cationized guar gum derivative; and (d) a diallyl quaternary ammonium salt polymer or a diallyl quaternary ammonium salt/acrylamide copolymer.

Hereinafter, the (a) cationic group-containing copolymer of the component (D) is described in detail.

(i) Nonionic Group-containing Vinyl Monomers

Specific examples of the monomer represented by the general formula (1) include (meth)acrylamide, N-methyl(meth) acrylamide, N,N-dimethyl (meth)acrylamide, N,N-diethyl (meth)acrylamide, N-n-propyl(meth)acrylamide, N-isopropyl(meth)acrylamide, N-t-butyl(meth)acrylamide, N-isobutyl(meth)acrylamide and N-hydroxypropyl(meth) acrylamide. Examples of the monomer represented by the general formula (II) include N-(meth)acryloylmorpholine.

(ii) Cationic Group-containing Vinyl Monomers

Specific examples of the monomer represented by the above general formula (III) include acid-neutralized products prepared by neutralizing the following compounds with an acid or quaternary ammonium salts prepared by quaternizing the following compounds with a quaternizing agent: dialkylamino group-containing (meth)acrylic acid esters or (meth) acrylamides such as dimethylaminoethyl (meth)acrylate, diethylaminoethyl (meth)acrylate, dipropylaminoethyl (meth)acrylate, diisopropylaminoethyl (meth)acrylate, dibutylaminoethyl (meth)acrylate, diisobutylaminoethyl (meth) acrylate, di-t-butylaminoethyl (meth)acrylate, dimethylaminopropyl(meth)acrylamide, diethylaminopropyl(meth) acrylamide, dipropylaminopropyl(meth)acrylamide, diisopropylaminopropyl(meth)acrylamide, dibutylaminopropyl(meth)acrylamide, diisobutylaminopropyl(meth)acrylamide, and di-t-butylaminopropyl(meth)acrylamide.

Specific examples of the monomer represented by the general formula (IV) include diallyl-type quaternary ammonium salts such as dimethyldiallylammonium chloride and diethyldiallylammonium chloride.

Examples of the acids suitable for preparing the above-mentioned acid-neutralized products include: inorganic acids such as hydrochloric acid, sulfuric acid, nitric acid and phosphoric acid; and organic acids having 1 to 22 carbon atoms in total such as acetic acid, formic acid, maleic acid, fumaric acid, citric acid, tartaric acid, adipic acid, sulfamic acid, toluenesulfonic acid, lactic acid, pyrrolidone-2-carboxylic acid, succinic acid, propionic acid and glycolic acid. Examples of the quaternizing agent suitable for preparing the above-mentioned quaternary ammonium salts include: alkyl halides having 1 to 8 carbon atoms such as methyl chloride, ethyl chloride, methyl bromide and methyl iodide; and common alkylation agents such as dimethyl sulfate, diethyl sulfate and di-n-propyl sulfate.

More preferable examples of the monomer represented by the above general formula (III) or (IV) include: quaternary ammonium salts prepared by quaternizing, with the above-mentioned quaternizing agents, dimethylaminoethyl (meth)acrylate, diethylaminoethyl (meth)acrylate, dimethylaminopropyl(meth)acrylamide or diethylaminopropyl(meth)acrylamide; or dimethyldiallylammonium chloride. The acid-neutralized product monomers undergo the dissociation of the acid used for neutralization depending on the pH and others of the system concerned to modify the polymer structure, and hence have a drawback such that the viscosity stability is low. Also from this viewpoint, quaternary ammonium salt-type monomers are more preferable.

(iii) Crosslinkable Vinyl Monomers

Examples of the crosslinkable vinyl monomer include: (meth)acrylates of polyhydric alcohols such as ethylene glycol di(meth)acrylate, diethylene glycol di(meth)acrylate, polyethylene glycol di(meth)acrylate, propylene glycol di(meth)acrylate, dipropylene glycol di(meth)acrylate, polypropylene glycol di(meth)acrylate, 1,2-butylene glycol di(meth)acrylate, 1,3-butylene glycol di(meth)acrylate, neopentyl glycol di(meth)acrylate, glycerin di(meth)acrylate, glycerin tri(meth)acrylate, trimethylolpropane tri(meth)acrylate, and pentaerythritol tetra(meth)acrylate; acrylamides such as N-methylallylacrylamide, N-vinylacrylamide, N,N'-methylenebis(meth)acrylamide and bisacrylamide acetate; divinyl compounds such as divinylbenzene, divinyl ether and divinylethylene urea; polyallyl compounds such as diallyl phthalate, diallyl maleate, diallylamine, triallylamine, triallylammonium salt, allyl-etherified pentaerythritol, and allyl-etherified sucrose having in the molecule thereof at least two allyl ether units; and (meth)acrylates of unsaturated alcohols such as vinyl (meth)acrylate, allyl (meth)acrylate, and 2-hydroxy-3-acryloyloxypropyl (meth)acrylate.

Preferable among these crosslinkable monomers is ethylene glycol di(meth)acrylate, polyethylene glycol di(meth)acrylate, divinylbenzene, pentaerythritol triallyl ether or pentaerythritol tetraallyl ether.

(iv) Other Vinyl Monomers

The cationic group-containing copolymer of the component (A) can include, as the constituent components thereof, in addition to the above-mentioned three types of vinyl monomers as the essential constituent units, other vinyl monomers capable of copolymerizing with these essential vinyl monomers. Examples of the other vinyl monomers include (meth)acrylic acid derivatives such as methyl (meth)acrylate, ethyl (meth)acrylate, n-propyl (meth)acrylate, isopropyl (meth)acrylate, n-butyl (meth)acrylate, isobutyl (meth)acrylate, t-butyl (meth)acrylate, n-pentyl (meth)acrylate, neopentyl (meth)acrylate, cyclopentyl (meth)acrylate, n-hexyl (meth)acrylate, cyclohexyl (meth)acrylate, n-octyl (meth)acrylate, isooctyl (meth)acrylate, 2-ethylhexyl (meth)acrylate, n-decyl (meth)acrylate, isodecyl (meth)acrylate, lauryl (meth)acrylate, tridecyl (meth)acrylate, stearyl (meth)acrylate, isostearyl (meth)acrylate, behenyl (meth)acrylate, phenyl (meth)acrylate, toluoyl (meth)acrylate, xylyl (meth)acrylate, benzyl (meth)acrylate, 2-ethoxyethyl (meth)acrylate, 2-butoxy (meth)acrylate, 2-phenoxy (meth)acrylate, 3-methoxypropyl (meth)acrylate and 3-ethoxypropyl (meth)acrylate.

The above-mentioned other vinyl monomers each are preferably used in a proportion of 30% by weight or less and more preferably in a proportion of 15% by weight or less in the total amount of all the monomers constituting the cationic group-containing copolymer.

(v) Cationic Group-containing Copolymer

The mixing ratio between the nonionic group-containing vinyl monomer (a1) and the cationic group-containing vinyl monomer (a2), both being the monomers to form the cationic group-containing copolymer, in terms of the molar ratio (a1)/(a2), is preferably 2/98 to 98/2, and more preferably 40/60 to 97/3. When this molar ratio is large, the development of thixotropic behavior becomes easy, and when this molar ratio is small, the viscosity retention at low shear rate becomes easy; thus, for the purpose of developing both of these properties, the (a1)/(a2) ratio preferably falls within the above-mentioned range.

The proportion of the crosslinkable vinyl monomer (a3) is preferably 0.002 to 5% by weight, and more preferably 0.002% by weight or more and less than 0.1% by weight in relation to the total amount of all the monomers. When the proportion of the monomer (a3) is 0.002% by weight or more, the viscosity of a hydrogel formed from the cationic group-containing copolymer is sufficient, and when the proportion of the monomer (a3) is 5% by weight or less, the hydrogel exhibits soft feeling and satisfactory slippability.

Examples of a preferable embodiment of the (a) cationic group-containing copolymer of the component (D) of the present invention include the N,N-dimethylaminoethyl methacrylate diethyl sulfate/N,N-dimethylacrylamide/polyethylene glycol dimethacrylate copolymer represented by the following formula:

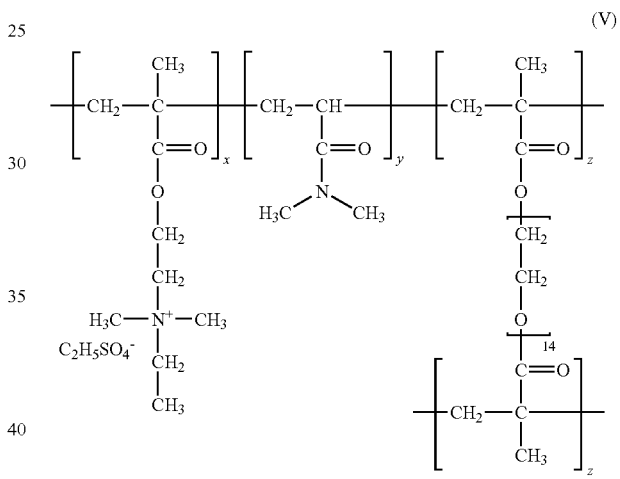

wherein, in terms of molar ratio, x/y=1/9 to 5/5, (X+Y+z)/z=1/0.1 to 1/0.002.

Commercially available examples of the cationic group-containing copolymer include Sofcare KG-301W (manufactured by Kao Corp.; x:y:z=30:70:0.0038 (molar ratio)), Sofcare KG-101E (manufactured by Kao Corp.; x:y:z=10:90:0.0035 (molar ratio)) and Sofcare KG-301P (manufactured by Kao Corp.; x:y:z=30:70:0.0038 (molar ratio)).

Hereinafter, the (b) cationized cellulose derivative of the component (D) is described in detail.

As the (b) cationized cellulose derivative, the compound represented by the following general formula (VI) is preferable:

wherein in formula (VI), A represents the residue of the anhydroglucose unit, "a" is an integer of 50 to 20000, and each $R^{21}$ represents a substituent represented by the following general formula (VII):

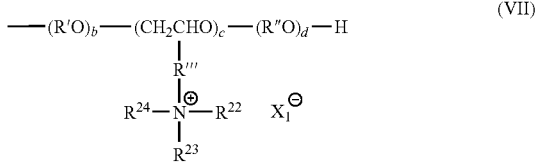

(VII)

wherein in formula (VII), R' and R" each represent an alkylene group having 2 or 3 carbon atoms, b represents an integer of 0 to 10, c represents an integer of 0 to 3, d represents an integer of 0 to 10, R''' represents an alkylene or hydroxyalkylene group having 1 to 3 carbon atoms, $R^{22}$, $R^{23}$ and $R^{24}$ are the same or different and each represent an alkyl, aryl or aralkyl group having up to 10 carbon atoms, or may form a heterocyclic ring including the nitrogen atom in the formula, and $X_1^-$ represents an anion (for example, a chloride, bromide, iodide, sulfate, sulfonate, methylsulfate, phosphate or nitrate ion).

The cation substitution degree of the cationized cellulose, namely, the average value of c per anhydroglucose unit is 0.01 to 1, and preferably 0.02 to 0.5. Additionally, the sum b+d is 1 to 3 on average. The substitution degree of 0.01 or less is not sufficient, and the substitution degree may be 1 or more; however, the substitution degree is preferably 1 or less from the viewpoint of the reaction yield. $R^{22}$, $R^{23}$ and $R^{24}$ are preferably, for example, such that these groups are all a $CH_3$ group, or two of them are short chain alkyl groups such as a $CH_3$ group and the remaining one of them is a long chain alkyl group having 10 to 20 carbon atoms. The molecular weight of the cationized cellulose to be used here is approximately between 100000 to 8000000.

Commercially available examples of the cationized cellulose include Poise C-60H (manufactured by Kao Corp.) and Poise C-80H (manufactured by Kao Corp.), and Polymer JR-400 (manufactured by Dow Chemical Co.).

Hereinafter, the (c) cationized guar gum derivative of the component (D) is described in detail.

As the (c) cationized guar gum derivative, the compound represented by the following general formula (VIII) is preferable:

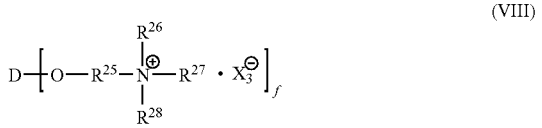

(VIII)

wherein in formula (VIII), D represents a guar gum residue, $R^{25}$ represents an alkylene or hydroxyalkylene group, $R^{26}$, $R^{27}$ and $R^{28}$ are the same or different and each represent an alkyl, aryl or aralkyl group having 10 or less carbon atoms, or may form a heterocyclic ring including the nitrogen atom in the formula, $X_3^-$ represents an anion (for example, a chloride, bromide, iodide, sulfate, sulfonate, methylsulfate, phosphate or nitrate ion), and f represents a positive integer.

The cation substitution degree of the cationized guar gum derivative is such that the cation group is introduced into the sugar unit preferably in a proportion of 0.01 to 1, and more preferably 0.02 to 0.5. Cationic polymers belonging to this type are described in JP-A-58-35640 and JP-A-60-46158, and JP-A-58-53996; commercially available examples of such cationic polymers include a product available under a trade name of Jaguar from Rhodia Inc., in particular, Jaguar C-13C, and additionally, Rabole gum CG-M manufactured by Dainippon Sumitomo Pharma Co., Ltd.

Hereinafter, the (d) diallyl quaternary ammonium salt polymer or diallyl quaternary ammonium salt/acrylamide copolymer of the component (D) is described in detail.

As the (d) diallyl quaternary ammonium salt polymer or diallyl quaternary ammonium salt/acrylamide copolymer, the compound represented by the following general formula (IX) or (X) is preferable:

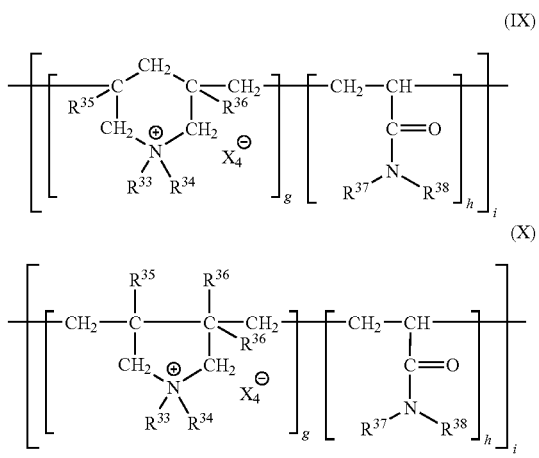

wherein in formulas (IX) and (X), $R^{33}$ and $R^{34}$ are the same or different, and each represent a hydrogen atom, an alkyl group having 1 to 18 carbon atoms, a phenyl group, an aryl group, a hydroxyalkyl group, an amidealkyl group, a cyanoalkyl group, an alkoxyalkyl group or a carboalkoxyalkyl group, $R^{35}$, $R^{36}$, $R^{37}$ and $R^{38}$ are the same or different and each represent a hydrogen atom, a lower alkyl group having 1 to 3 carbon atoms or a phenyl group, $X_4^-$ represents an anion (for example, a chloride, bromide, iodide, sulfate, sulfonate, methylsulfate or nitrate ion), g represents an integer of 1 to 50, h represents an integer of 0 to 50, and i represents an integer of 150 to 8000.

The molecular weight of the diallyl quaternary ammonium salt/acrylamide copolymer is recommended to fall approximately within a range from 30000 to 2000000, and preferably from 100000 to 1000000.

Commercially available examples of such a copolymer include the products available under the trade name of Merquat from Nalco Co., in particular, Merquat 100, Merquat 550 and Merquat 3331.

One or more types of the component (D) may be used. The content of the component (D) in the detergent composition of the present invention is, from the viewpoint of the foam quality improvement effect, preferably 0.01 to 5% by weight, more preferably 0.05 to 2.5% by weight and even more preferably 0.1 to 2.5% by weight in the whole composition.

The detergent composition of the present invention can further enhance the initial foaming by further mixing a nonionic surfactant (E) (hereinafter referred to as the component (E)) in the composition. It is to be noted that the present invention excludes the compounds having the structures of the general formulas (2) and (3) from the nonionic surfactants as the component (E).

Examples of the component (E) include an alkyl glycoside, an alkyl polyglycoside, a sucrose fatty acid ester, a polyglycerin fatty acid ester, a fatty acid alkanol amide, an alkyl amine oxide, and a fatty acid ester of a polyhydric alcohol. Preferable among these are a fatty acid alkanol amide, an alkyl glycoside and an alkyl polyglycoside, and more preferable are an alkyl glycoside and an alkyl polyglycoside. Further, when the component (E) is an alkyl glycoside or an alkyl polyglycoside, such a compound brings about moderate grating feeling at the time of rising, and hence can suppress the sliminess inherent to a formulation including the component (A) so as to impart freshening feeling.

As an alkyl glycoside or an alkyl polyglycoside, a compound represented by the following general formula (5) is preferable:

$$R^9\text{—}O\text{—}(R^{10}O)_s\text{-}(G)_t \quad (5)$$

wherein $R^9$ represents a straight chain or branched chain, alkyl, alkenyl or alkylphenyl group having 8 to 18 carbon atoms, $R^{10}$ represents an alkylene group having 2 to 4 carbon atoms, G represents a reducing sugar having 5 or 6 carbon atoms, an average addition number of moles s represents a number of 0 to 10, and the average sugar polymerization degree t represents a number of 1 to 10.

Among others, $R^9$ is preferably a straight chain or branched chain, alkyl or alkenyl group having 10 to 14 carbon atoms, the reducing sugar represented by G is preferably glucose, galactose or fructose, and more preferably glucose. The average sugar polymerization degree t is preferably 1 to 4. It is desirable to select the average sugar polymerization degree t in view of the physical properties derived from the alkyl or alkenyl group represented by $R^9$; for example, when $R^9$ is an alkyl group having 8 to 11 carbon atoms, it is preferable to select 1 to 1.4 for t, and when $R^9$ is an alkyl group having 12 to 14 carbon atoms, it is preferable to select 1.5 to 4.0 for t. Specific examples of such an alkyl glycoside include decyl glucoside and lauryl glucoside.

One or more types of the component (E) may be used. The content of the component (E) in the detergent composition of the present invention is, from the viewpoint of the foamability enhancement, preferably 0.01 to 20% by weight, more preferably 0.05 to 20% by weight and even more preferably 0.1 to 15% by weight in the whole composition.

The detergent composition of the present invention can be used as it is or as diluted with water. For example, the detergent composition of the present invention can be used as skin detergents such as a face wash and a body shampoo, or hair detergents such as a shampoo. In these detergent compositions, optional components may be mixed according to the purposes of the individual compositions. Examples of the optional components as referred to herein include anionic surfactants other than the component (A), amphoteric surfactants and cationic surfactants, and conditioning components other than the component (B), usually mixed in these detergent compositions.

The detergent composition of the present invention is preferably used as a face wash or a skin detergent. It is to be noted that when the detergent composition of the present invention is used as a face wash or a skin detergent, it is preferable not to mix any silicone oil therein.

Examples of the anionic surfactants other than the component (A) include fatty acid salts, phosphoric acid ester salts, sulfosuccinic acid surfactants, polyoxyalkylenealkylamide ether sulfates, monoglyceride sulfates, olefinsulfonates, alkanesulfonates, acylated isethionates, acylated amino acid salts, polyoxyalkylenealkyl ether phosphates, and polyoxyalkylenealkyl ether acetates.

Examples of the amphoteric surfactant include amidobetaine surfactants, amidoamino acid surfactants, carbobetaine surfactants, sulfobetaine surfactants, amidosulfobetaine surfactants, imidazolinium betaine surfactants and phosphobetaine surfactants. More preferable among these are alkylcarboxymethylhydroxyethyl imidazolinium betaines, fatty acid amide propylbetaines, and alkylhydroxysulfobetaines. The fatty acid amide propylbetaines and alkylhydroxysulfobetaines each preferably have an alkyl group having 8 to 18 carbon atoms, and more preferably 10 to 16 carbon atoms; even more preferable examples include lauric acid amide propylbetaine, palm kernel oil fatty acid amide propylbetaine, coconut oil fatty acid amide propylbetaine, and laurylhydroxysulfobetaine. The content of each of these amphoteric surfactants is, from the viewpoint of the foamability, preferably 0.1 to 10% by weight, more preferably 0.5 to 10% by weight and even more preferably 0.5 to 8% by weight in the detergent composition of the present invention.

Examples of the cationic surfactant include quaternary ammonium salts represented by the following general formula (4):

$$R^5\text{—}\overset{R^6}{\underset{R^8}{N^+}}\text{—}R^7 \; Z^- \quad (4)$$

wherein at least one of $R^5$, $R^6$, $R^7$ and $R^8$ represents an alkoxy, alkenyloxy or alkanoylamino group having 8 to 28 carbon atoms in total, or an alkyl or alkenyl group optionally substituted with an alkenoylamino group, having 8 to 28 carbon atoms in total; each of the rest of these groups represents a benzyl group, an alkyl group having 1 to 5 carbon atoms, a hydroxyalkyl group or a polyoxyethylene group having a total addition number of moles of 10 or less, and $Z^-$ represents a halide ion or an organic anion.

Examples of the conditioning component include: higher alcohols such as lauryl alcohol, cetyl alcohol and stearyl alcohol; and oils such as silicone and silicone derivatives, lanolin, squalene, hydrocarbons, protein derivatives, and fatty acid esters of polyethylene glycol. More preferable among these conditioning components is lauryl alcohol. From the viewpoints of the improvement of feeling of foam and the storage stability, these conditioning components each are included in the detergent composition of the present invention preferably in a content of 0.05 to 5% by weight, more preferably 0.1 to 5% by weight and even more preferably 0.1 to 2% by weight.

For example, the following other components commonly used in detergent compositions can be mixed according to need within ranges that do not impair the advantageous effects of the present invention: water-soluble polymers such as polysaccharides including methyl cellulose, hydroxyethyl cellulose, carboxyvinyl polymer and xanthan gum; viscosity modifiers such as polyoxyalkylene sorbitan ester, polyoxyethylene glycol distearate and ethanol; chelating agents such as ethylenediaminetetraacetic acid (EDTA) and phosphonic acid salts; antiseptic agents such as methylparaben and butylparaben; effective components such as vitamins and the precursors thereof; animal and plant extracts and the derivatives thereof such as lecithin and gelatin; fine powders of polymers such as nylon and polyethylene; antiphlogistic agents such as dipotassium glycyrrhizinate; bactericides and antidandruff agents such as triclosan, trichlorocarban, octopirox and zinc pyrithione; antioxidant agents such as dibutylhydroxytoluene; pearling agents, ultraviolet absorbers; pH modifiers; colorants; perfumes; and water.

The detergent composition of the present invention can be produced by mixing under stirring at temperatures ranging from 15 to 80° C., for example, the components (A), (B) and (C), and additionally the components (D), (E) and other components according to need. The formulation of the detergent composition of the present invention is not particularly limited, but is preferably a liquid, a paste or a cream. At the time of production, it is preferable to use a solvent, and water is preferable as solvent.

EXAMPLES

Hereinafter, the present invention is described in more detail with reference to Examples.

Examples 1 to 19 and Comparative Examples 1 to 16

<Preparation Method>
Each of the body detergents shown in Tables 1 and 2 were prepared by mixing the components (B) and (C) in an aqueous solution of the component (A), and additionally the components (D) and (E) and other components according to need, and by heating the solution under stirring at 70° C. for 2 hours.

<Evaluation Methods>
(Foam Viscosity)
With 10 mL of 4° DH hard water, 1 mL of each of the body detergents thus prepared was diluted; and the diluted solution was foamed by a hand-washing operation for 20 seconds. The foam thus prepared was placed in a 50-mL beaker, and the foam viscosity (mPa·s) after 30 seconds at 25° C. was measured with a B-type viscometer (manufactured by Tokyo Keiki Co., Ltd.). In this measurement, the rotation number was 12 rpm, and a No. 3 rotor was used.

(Organoleptic Evaluation of Foam Quality)
With 10 mL of 4° DH hard water, 1 mL of each of the body detergents thus prepared was diluted; and the diluted solution was foamed by a hand-washing operation for 20 seconds. The foam thus prepared was subjected to an organoleptic evaluation. The organoleptic evaluation was conducted by a panel of 10 experts on the creaminess degree of the foam with reference to a soap (15% aqueous solution of lauric acid/myristic acid/palmitic acid=6/4.5/4.5) as a standard as follows: when 9 or more of the 10 experts judged the creaminess degree as comparable with that of the soap, the creaminess degree was graded as "A"; when 7 to 8 of 10 experts judged as comparable, it was graded as "B"; when 5 to 6 of 10 experts judged as comparable, it was graded as "C"; when 3 to 4 of 10 experts judged as comparable, it was graded as "D"; and when 2 or less of 10 experts judged as comparable, it was graded as "E."

(Evaluation of Foam Amount)
With 10 mL of 4° DH hard water, 1 mL of each of the body detergents thus prepared was diluted; and the diluted solution was foamed by a hand-washing operation for 20 seconds. The foam thus prepared was subjected to an evaluation of the foam amount. The evaluation of the foam amount was conducted by a panel of 10 experts on the foam amount with reference to the soap (15% aqueous solution of lauric acid/myristic acid/palmitic acid=6/4.5/4.5) as a standard as follows: when 9 or more of the 10 experts judged the foam amount as equal to or more than that of the soap, the foam amount was graded as "A"; when 7 to 8 of 10 experts judged as equal to or more, it was graded as "B"; when 5 to 6 of 10 experts judged as equal to or more, it was graded as "C; when 3 to 4 of 10 experts judged as equal to or more, it was graded as "D; when 2 or less of 10 experts judged as equal to or more, it was graded as "E;

(Storage Stability (1))
In a 50-mL glass vessel (the internal diameter: 3.2 cm) 40 mL of each of the body detergents thus prepared was placed and stored at room temperature (25° C.) for 6 months, and then the presence/absence of the separation was identified.

(Storage Stability (2))
In a 50-mL glass vessel (the internal diameter: 3.2 cm) 40 mL of each of the body detergents thus prepared was placed, and was subjected to a cycle test in which the temperature was changed in a range from −28 to 40° C. (one round trip/8 hours) for 14 days; and on completion of the cycle test, the presence/absence of the separation was identified.

TABLE 1

| Component (% by weight) | | Examples | | | | | | | | |
|---|---|---|---|---|---|---|---|---|---|---|
| | | 1 | 2 | 3 | 4 | 5 | 6 | 7 | 8 | 9 |
| Component (A) | Sodium polyoxyethylene(2)lauryl ether sulfate[1] | 15.3 | 15.3 | 15.3 | 15.3 | 15.3 | 14.2 | 14.2 | 15.3 | 15.3 |
| Component (B) | Myristyl alcohol[2] | 2.0 | 2.0 | 2.0 | 2.0 | 2.0 | 1.8 | 1.8 | 2.0 | 2.0 |
| Component (C) | 2-Ethylhexyl glyceryl ether (C-2)[3] | 1.5 | — | — | 1.0 | 1.0 | 1.5 | 1.5 | 1.5 | 1.5 |
| | Isodecyl glyceryl ether (C-2)[4] | — | 1.5 | — | — | — | — | — | — | — |
| | Polyoxypropylene(2.7) monooctyl ether (C-1)[5] | — | — | 1.5 | — | — | — | — | — | — |
| Component (D) | N,N-dimethylacrylamide/polyethylene glycol dimethacrylate copolymer[6] | — | — | — | — | — | — | — | 0.25 | — |
| | Diallyl quaternary ammonium salt/acrylamide copolymer[7] | — | — | — | — | — | 0.18 | 0.18 | — | 0.25 |
| Component (E) | Decyl glucoside[8] | — | — | — | — | — | 2.0 | — | — | — |
| | Coconut oil fatty acid N-methyl-monoethanolamide[9] | — | — | — | 0.6 | — | — | — | — | — |
| | Ethyl alcohol[10] | — | — | — | — | — | — | — | — | — |
| | Behenyl alcohol[11] | — | — | — | — | — | — | — | — | — |
| | Lauric acid amide propylbetaine[12] | — | — | — | — | 0.4 | — | — | — | — |
| | Laurylhydroxysulfobetaine[13] | — | — | — | — | — | 1.0 | 1.0 | — | — |
| | Ion-exchanged water | 81.2 | 81.2 | 81.2 | 81.1 | 81.3 | 79.3 | 81.3 | 81.0 | 81.0 |
| | Total | 100 | 100 | 100 | 100 | 100 | 100 | 100 | 100 | 100 |
| | (A)/(B) | 88/12 | 88/12 | 88/12 | 88/12 | 94/6 | 89/11 | 89/11 | 88/12 | 88/12 |
| | (A)/(C) | 91/9 | 91/9 | 91/9 | 94/6 | 94/6 | 90/10 | 90/10 | 91/9 | 91/9 |
| | (B)/(C) | 57/43 | 57/43 | 57/43 | 67/33 | 67/33 | 54/46 | 54/46 | 57/43 | 57/43 |

TABLE 1-continued

| | | | | | | | | | | |
|---|---|---|---|---|---|---|---|---|---|---|
| Foam viscosity (mPa·s) | 3450 | 4200 | 5020 | 3250 | 3250 | 17200 | 14800 | 20000 | 16800 | |
| Organoleptic evaluation of foam quality | A | A | A | B | B | A | A | A | A | |

| | Component (% by weight) | Comparative Examples | | | | | | | | | |
|---|---|---|---|---|---|---|---|---|---|---|---|
| | | 1 | 2 | 3 | 4 | 5 | 6 | 7 | 8 | 9 | 10 |
| Component (A) | Sodium polyoxyethylene(2)lauryl ether sulfate[1] | 15.3 | 15.3 | 15.3 | 15.3 | 15.3 | 15.3 | 15.3 | 15.3 | 17.6 | 14.2 |
| Component (B) | Myristyl alcohol[2] | — | — | — | — | — | — | — | — | — | — |
| Component (C) | 2-Ethylhexyl glyceryl ether (C-2)[3] | — | 1.5 | 1.5 | 1.5 | — | — | — | — | — | 1.5 |
| | Isodecyl glyceryl ether (C-2)[4] | — | — | — | — | 1.5 | — | — | — | — | — |
| | Polyoxypropylene(2.7) monooctyl ether (C-1)[5] | — | — | — | — | — | 1.5 | — | — | — | — |
| Component (D) | N,N-dimethylacrylamide/ polyethylene glycol dimethacrylate copolymer[6] | | | | | | | | | | |
| | Diallyl quaternary ammonium salt/acrylamide copolymer[7] | — | — | — | — | — | — | — | — | — | — |
| Component (E) | Decyl glucoside[8] | — | — | — | — | — | — | — | — | — | 2.0 |
| | Coconut oil fatty acid N-methyl-monoethanolamide[9] | — | — | — | — | — | — | 1.2 | — | — | — |
| | Ethyl alcohol[10] | — | 1.5 | — | — | — | — | — | — | — | — |
| | Behenyl alcohol[11] | — | — | 1.5 | — | — | — | 1.5 | — | — | — |
| | Lauric acid amide propylbetaine[12] | — | — | — | — | — | — | — | 4.0 | — | — |
| | Laurylhydroxysulfobetaine[13] | — | — | — | — | — | — | — | — | 4.0 | 1.0 |
| | Ion-exchanged water | 84.7 | 81.7 | 81.7 | 83.2 | 83.2 | 83.2 | 82.0 | 80.7 | 78.4 | 81.3 |
| | Total | 100 | 100 | 100 | 100 | 100 | 100 | 100 | 100 | 100 | 100 |
| | (A)/(B) | — | — | — | — | — | — | — | — | — | — |
| | (A)/(C) | — | 91/9 | 91/9 | 91/9 | 91/9 | 91/9 | — | — | — | 90/10 |
| | (B)/(C) | — | — | — | — | — | — | — | — | — | — |
| | Foam viscosity (mPa·s) | 500 | 350 | 368 | 360 | 380 | 316 | 364 | 384 | 480 | 320 |
| | Organoleptic evaluation of foam quality | D | E | E | E | E | E | E | E | D | E |

[1]Emal 227; manufactured by Kao Corp.; in the general formula (1), $R^1$: lauryl, n = 2, M = sodium
[2]Kalcol 4098; manufactured by Kao Corp.
[3]In the general formula (3), $R^4$: 2-ethylhexyl
[4]In the general formula (3), $R^4$: isodecyl
[5]In the general formula (2), $R^2$: n-octyl, n: 2.7, $R^3$: hydrogen atom
[6]Sofcare KG-301W; manufactured by Kao Corp.
[7]Merquat 550; manufactured by Nalco Co.
[8]Mydol 10; manufactured by Kao Corp.
[9]Aminon C-11S; manufactured by Kao Corp.
[10]Special-grade ethanol; manufactured by Wako Pure Chem. Ind., Ltd.
[11]Kalcol 220-80; manufactured by Kao Corp.
[12]Amphitol 20AB; manufactured by Kao Corp.
[13]Amphitol 20HD; manufactured by Kao Corp.

As can be seen from the results shown in Table 1, the body detergents of the present invention including the component (B) exhibited a high foam viscosity even when any one of the component (C) was used (Examples 1 to 3); and creamy foam was obtained even when another nonionic surfactant as the component (E) is added (Examples 4 and 6) or an amphoteric surfactant was added (Example 5). However, the foam viscosity was approximately 500 mPa·s and the foam quality was not improved in Comparative Example 2 in which the component (B) had an extremely short carbon chain, in Comparative Example 3 in which the component (B) had an extremely long carbon chain, and Comparative Examples 1 and 4 to 10 in each of which no component (B) was included.

TABLE 2

| | | Examples | | | | | | | | | |
|---|---|---|---|---|---|---|---|---|---|---|---|
| | Component (% by weight) | 10 | 11 | 12 | 13 | 14 | 15 | 16 | 17 | 18 | 19 |
| Component (A) | Sodium polyoxyethylene(2)lauryl ether sulfate[1] | 15.3 | 15.3 | 15.3 | 15.3 | 15.3 | 15.3 | 17.2 | 18 | 20 | 14.2 |
| Component (B) | Myristyl alcohol[2] | 2 | 2 | 1.6 | 1.6 | 2.5 | 2 | 2 | 2 | 2 | 1.8 |
| Component (C) | 2-Ethylhexyl glyceryl ether (C-2)[3] | 1.5 | 2 | 1.6 | 2 | 2 | 0.8 | 0.8 | 0.6 | 2 | 1.5 |
| | Ion-exchanged water | 81.2 | 80.7 | 81.5 | 81.1 | 80.2 | 81.9 | 80.0 | 79.4 | 76.0 | 82.5 |
| | Total | 100 | 100 | 100 | 100 | 100 | 100 | 100 | 100 | 100 | 100 |
| | (A)/(B) | 88/12 | 88/12 | 91/9 | 91/9 | 86/14 | 88/12 | 90/10 | 90/10 | 91/9 | 89/11 |

TABLE 2-continued

|  | | | | | | | | | | |
|---|---|---|---|---|---|---|---|---|---|---|
| (A)/(C) | 91/9 | 88/12 | 91/9 | 88/12 | 88/12 | 95/5 | 96/4 | 97/3 | 91/9 | 90/10 |
| (B)/(C) | 57/43 | 50/50 | 50/50 | 44/56 | 56/44 | 71/29 | 71/29 | 77/23 | 50/50 | 54/46 |
| Evaluation of foam amount | B | A | B | A | B | B | B | B | A | B |
| Organoleptic evaluation of foam quality | A | B | A | B | A | A | A | A | B | A |
| Storage stability (1) (separation) | Absent | Absent | Absent | Absent | Absent | Absent | Absent | Absent | Absent | Absent |
| Storage stability (2) (separation) | Absent | Absent | Absent | Absent | Absent | Absent | Absent | Absent | Absent | Absent |

| | | | Comparative Examples | | | | | |
|---|---|---|---|---|---|---|---|---|
| | Component (% by weight) | | 11 | 12 | 13 | 14 | 15 | 16 |
| Component (A) | Sodium polyoxyethylene(2)lauryl ether sulfate[1] | | 12 | 13 | 8 | 12 | 19 | 16 |
| Component (B) | Myristyl alcohol[2] | | 6 | 6 | 8 | 1 | 0.02 | 0.04 |
| Component (C) | 2-Ethylhexyl glyceryl ether (C-2)[3] | | 2 | 1 | 4 | 0.6 | 0.98 | 3.96 |
| | Ion-exchanged water | | 80.0 | 80.0 | 80.0 | 86.4 | 80.0 | 80.0 |
| | Total | | 100 | 100 | 100 | 100 | 100 | 100 |
| | (A)/(B) | | 67/33 | 68/32 | 50/50 | 92/8 | 99.9/0.1 | 99.8/0.2 |
| | (A)/(C) | | 86/14 | 93/7 | 67/33 | 95/5 | 95/5 | 80/20 |
| | (B)/(C) | | 75/25 | 86/14 | 67/33 | 62/38 | 2/98 | 1/99 |
| | Evaluation of foam amount | | E | E | E | B | A | A |
| | Organoleptic evaluation of foam quality | | D | D | D | C | E | E |
| | Storage stability (1) (separation) | | Present | Present | Present | Absent | Absent | Absent |
| | Storage stability (2) (separation) | | Present | Present | Present | Absent | Absent | Absent |

[1]Emal 227; manufactured by Kao Corp.; in the general formula (1), $R^1$: lauryl, n = 2, M = sodium
[2]Kalcol 4098; manufactured by Kao Corp.
[3]In general the formula (3), $R^4$: 2-ethylhexyl As can be seen from the results shown in Table 2, the body detergents of the present invention including the components (A), (B) and (C) were not able to attain sufficient advantageous effects with prescriptions having proportions other than specific proportions of the components (A), (B) and (C); in each of Comparative Examples 11 to 13, the amount of the component (B) was excessive, and hence the foamability was remarkably degraded and the creaminess of the foam quality was also insufficient; additionally, in each of Comparative Examples 14 to 16, the component (B) was deficient, and hence no creamy foam was obtained.

Example 20

A body shampoo having the following composition was prepared.

| (Component) | (% by weight) |
|---|---|
| Sodium polyoxyethylene(2)lauryl ether sulfate (Emal 227; manufactured by Kao Corp.) | 15.0 |
| Myristyl alcohol (Kalcol 4098; manufactured by Kao Corp.) | 1.6 |
| 2-Ethylhexyl glyceryl ether | 1.6 |
| Laurylhydroxysulfobetaine (Amphitol 20HD; manufactured by Kao Corp.) | 1.0 |
| Cationized cellulose (Poise C-60H; manufactured by Kao Corp.) | 0.1 |
| Sodium chloride | 0.5 |
| Perfume, Methylparaben | q.s. |
| Purified water | Balance |
| Total | 100.0 |

The body shampoo of Example 20 was abundant in the foam amount, and the entire body was able to be washed with comfortable creamy foam.

Example 21

A face wash having the following composition was prepared.

| (Component) | (% by weight) |
|---|---|
| Sodium polyoxyethylene(2)lauryl ether sulfate (Emal 227; manufactured by Kao Corp.) | 52.6 |
| Myristyl alcohol (Kalcol 4098; manufactured by Kao Corp.) | 5.1 |
| 2-Ethylhexyl glyceryl ether | 4.6 |
| Laurylhydroxysulfobetaine (Amphitol 20HD; manufactured by Kao Corp.) | 3.5 |
| Glycerin | 1.0 |
| Sorbitol | 2.0 |
| N,N-dimethylaminoethyl methacrylate diethyl sulfate/N,N-dimethylacrylamide/polyethylene glycol dimethacrylate copolymer (Sofcare KG-301P; manufactured by Kao Corp.) | 0.6 |
| Perfume, Methylparaben | q.s. |
| Purified water | Balance |
| Total | 100.0 |

The face wash of Example 21 was rich in foam quality and produced a large amount of fine foam, and the face was able to be washed mildly with creamy foam quality.

Example 22

A hand soap having the following composition was prepared.

| (Component) | (% by weight) |
|---|---|
| Sodium polyoxyethylene(2)lauryl ether sulfate (Emal 227; manufactured by Kao Corp.) | 18.5 |
| Lauryl alcohol (Kalcol 2098; manufactured by Kao Corp.) | 0.5 |
| Myristyl alcohol (Kalcol 4098; manufactured by Kao Corp.) | 1.8 |
| Isodecyl glyceryl ether | 1.8 |
| Laurylhydroxysulfobetaine (Amphitol 20HD; manufactured by Kao Corp.) | 1.1 |
| Cationized cellulose (Poise C-60H; manufactured by Kao Corp.) | 0.1 |
| N,N-dimethylaminoethyl methacrylate diethyl sulfate/N,N-dimethylacrylamide/polyethylene glycol dimethacrylate copolymer (Sofcare KG-301P; manufactured by Kao Corp.) | 0.2 |
| Perfume, Methylparaben | q.s. |
| Purified water | Balance |
| Total | 100.0 |

The hand soap of Example 22 was satisfactory in foamability so as to quickly bring about fine foam.

Example 23

A body shampoo having the following composition was prepared.

| (Component) | (% by weight) |
|---|---|
| Sodium polyoxyethylene(2)lauryl ether sulfate (Emal 227; manufactured by Kao Corp.) | 14.2 |
| Myristyl alcohol (Kalcol 4098; manufactured by Kao Corp.) | 1.8 |
| 2-Ethylhexyl glyceryl ether | 1.5 |
| Laurylhydroxysulfobetaine (Amphitol 20HD; manufactured by Kao Corp.) | 1.0 |
| Decyl glucoside (Mydol 10; manufactured by Kao Corp.) | 2.0 |
| Dimethyldiallylammonium chloride/acrylamide copolymer (Merquat 550; manufactured by Nalco Co.) | 0.36 |
| Polyethylene glycol (Mw = 2500000) (Alcox E-100; manufactured by Meisei Chemical Co.) | 0.015 |
| Propylene glycol | 7.0 |
| Malic acid | 0.05 |
| Perfume, methylparaben | q.s. |
| Purified water | Balance |
| Total | 100.0 |

The body shampoo of Example 23 was excellent in initial foamability and brought about soft and creamy foam.

What is claimed is:

1. A detergent composition comprising the following components (A), (B) and (C):

(A) a polyoxyethylene alkyl ether sulfate or an alkyl sulfate represented by a general formula (1):

$$R^1O(CH_2CH_2O)_nSO_3M \tag{1}$$

wherein $R^1$ represents a straight chain or branched chain, alkyl or alkenyl group having 8 to 18 carbon atoms, an average addition number of moles n represents a number of 0 to 5, and M represents an alkali metal atom, an alkanolamine or ammonium;

(B) myristyl alcohol;

(C) one or more nonionic surfactants selected from the group consisting of an alkoxylate (C-1) represented by a general formula (2) and a glyceryl ether (C-2) represented by a general formula (3), (C-1) an alkoxylate represented by the general formula (2):

$$R^2O\text{-}(AO)_n\text{—}R^3 \tag{2}$$

wherein $R^2$ represents a straight chain or branched chain, alkyl or alkenyl group having 8 to 10 carbon atoms, AO represents an alkyleneoxy group having 2 to 4 carbon atoms, an average addition number of moles n represents a number of 0.5 or more and less than 4.0, and $R^3$ represents a hydrogen atom or a methyl group; and (C-2) a glyceryl ether represented by the general formula (3):

$$R^4\text{—}OCH_2\text{—}\underset{OH}{CH}\text{—}CH_2OH \tag{3}$$

wherein $R^4$ represents a straight chain or branched chain, alkyl or alkenyl group having 6 to 14 carbon atoms; wherein the weight ratio of the component (A) to the component (B) is (A)/(B)=91.5/8.5 to 80/20, the weight ratio of the component (A) to the component (C) is (A)/(C)=98/2 to 85/15, the weight ratio of the component (B) to the component (C) is (B)/(C)=90/10 to 30/70, and the content of the component (B) is 1.6 to 14% by weight.

2. The detergent composition according to claim 1, wherein the content of the component (A) is 5 to 70% by weight and the content of the component (C) is 0.05 to 14% by weight.

3. The detergent composition according to claim 1, wherein component (C-1) is present and AO in the component (C-1) is propyleneoxy.

4. The detergent composition according to claim 1, further comprising a cationic polymer (D).

5. The detergent composition according to claim 4, wherein the cationic polymer (D) is one or more selected from the group consisting of the following (a) to (d):

(a) a cationic group-containing copolymer obtained by a radical polymerization including as essential constituent monomers at least one nonionic group-containing vinyl monomer represented by a general formula (I) or (II), at least one cationic group-containing vinyl monomer represented by a general formula (III) or (IV), and at least one crosslinkable vinyl monomer having in the molecule thereof at least two groups selected from a vinyl group, an acryloyl group, a methacryloyl group and an allyl group:

$$\underset{CH_2=\overset{R^{11}}{C}\text{—}\overset{O}{\overset{\|}{C}}\text{—}\overset{R^{12}}{\overset{|}{N}}\text{—}R^{13}}{} \tag{I}$$

wherein $R^{11}$ represents a hydrogen atom or a methyl group, and $R^{12}$ and $R^{13}$ are the same or different and each represent a hydrogen atom or a straight chain or branched chain, alkyl or alkenyl group having 1 to 4 carbon atoms,

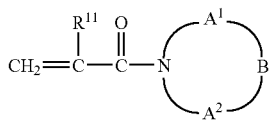

(II)

wherein $R^{11}$ represents the same meaning as above, $A^1$ and $A^2$ are the same or different and each represent a group represented by a formula —$(CH_2)_m$— with the proviso that m represents an integer of 2 to 6, and B represents a group —O— or —$CH_2$—,

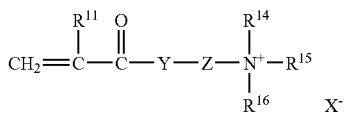

(III)

wherein $R^{11}$ represents the same meaning as above, $R^{14}$ and $R^{15}$ are the same or different and each represent an alkyl or alkenyl group having 1 to 4 carbon atoms, $R^{16}$ represents a hydrogen atom or an alkyl group having 1 to 4 carbon atoms, Y represents a group —O—, —NH—, —$CH_2$— or —O—$CH_2CH(OH)$—, Z represents a straight chain or branched chain alkylene group having 1 to 4 carbon atoms with the proviso that this group has 0 to 3 carbon atoms when Y is —$CH_2$—, and $X^-$ represents a conjugate base of an acid, a halide ion or an alkyl sulfate group having 1 to 4 carbon atoms,

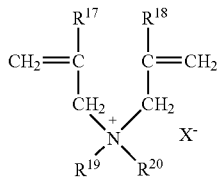

(IV)

wherein $R^{17}$ and $R^{18}$ are the same or different and each represent a hydrogen atom or a methyl group, $R^{19}$ and $R^{20}$ are the same or different and each represent a hydrogen atom or an alkyl group having 1 to 4 carbon atoms, and $X^-$ represents the same meaning as above;
(b) a cationized cellulose derivative;
(c) a cationized guar gum derivative; and
(d) a diallyl quaternary ammonium salt polymer or a diallyl quaternary ammonium salt/acrylamide copolymer.

6. The detergent composition claim 1, further comprising a nonionic surfactant (E) which is different from component (C).

7. The detergent composition according to claim 6, wherein the nonionic surfactant (E) is one or more selected from an alkyl glycoside or an alkyl polyglycoside.

8. The detergent composition according to claim 1, wherein the content of the component (A) is 30 to 70% by weight and the content of the component (C) is 2 to 14% by weight.

9. The detergent composition according to claim 1, wherein the content of the component (A) is 5 to 25% by weight, the content of the component (B) is 1.6 to 3% by weight and the content of the component (C) is 0.05 to 3% by weight.

10. A method for producing a detergent composition comprising the following components (A), (B) and (C):
(A) a polyoxyethylene alkyl ether sulfate or an alkyl sulfate represented by the general formula (1):

$$R^1O(CH_2CH_2O)_nSO_3M \quad (1)$$

wherein $R^1$ represents a straight chain or branched chain, alkyl or alkenyl group having 8 to 18 carbon atoms, the average addition number of moles n represents a number of 0 to 5, and M represents an alkali metal atom, an alkanolamine or ammonium;
(B) myristyl alcohol;
(C) one or more nonionic surfactants selected from the group consisting of an alkoxylate (C-1) represented by the general formula (2) and a glyceryl ether (C-2) represented by the general formula (3),
(C-1) an alkoxylate represented by the general formula (2):

$$R^2O\text{-}(AO)_n\text{—}R^3 \quad (2)$$

wherein $R^2$ represents a straight chain or branched chain, alkyl or alkenyl group having 8 to 10 carbon atoms, AO represents an alkyleneoxy group having 2 to 4 carbon atoms, the average addition number of moles n represents a number of 0.5 or more and less than 4.0, and $R^3$ represents a hydrogen atom or a methyl group; and
(C-2) a glyceryl ether represented by the general formula (3):

$$R^4\text{—}OCH_2\text{—}CH(OH)\text{—}CH_2OH \quad (3)$$

wherein $R^4$ represents a straight chain or branched chain, alkyl or alkenyl group having 6 to 14 carbon atoms,
comprising mixing components (A), (B), and (C) such that the weight ratio of the component (A) to the component (B) is (A)/(B)=91.5/8.5 to 80/20, the weight ratio of the component (A) to the component (C) is (A)/(C)=98/2 to 85/15, the weight ratio of the component (B) to the component (C) is (B)/(C)=90/10 to 30/70, and the content of the component (B) is 1.6 to 14% by weight.

11. A method comprising cleansing the skin or hair by using a composition comprising the following components (A), (B) and (C):
(A) a polyoxyethylene alkyl ether sulfate or an alkyl sulfate represented by the general formula (1):

$$R^1O(CH_2CH_2O)_nSO_3M \quad (1)$$

wherein $R^1$ represents a straight chain or branched chain, alkyl or alkenyl group having 8 to 18 carbon atoms, the average addition number of moles n represents a number of 0 to 5, and M represents an alkali metal atom, an alkanolamine or ammonium;
(B) myristyl alcohol;
(C) one or more nonionic surfactants selected from the group consisting of an alkoxylate (C-1) represented by the general formula (2) and a glyceryl ether (C-2) represented by the general formula (3),
(C-1) an alkoxylate represented by the general formula (2):

$$R^2O\text{-}(AO)_n\text{—}R^3 \quad (2)$$

wherein $R^2$ represents a straight chain or branched chain, alkyl or alkenyl group having 8 to 10 carbon atoms, AO represents an alkyleneoxy group having 2 to 4 carbon atoms, the average addition number of moles n represents a number of 0.5 or more and less than 4.0, and $R^3$ represents a hydrogen atom or a methyl group; and (C-2) a glyceryl ether represented by the general formula (3):

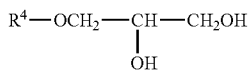   (3)

wherein $R^4$ represents a straight chain or branched chain, alkyl or alkenyl group having 6 to 14 carbon atoms, wherein the weight ratio of the component (A) to the component (B) is (A)/(B)=91.5/8.5 to 80/20, the weight ratio of the component (A) to the component (C) is (A)/(C)=98/2 to 85/15, the weight ratio of the component (B) to the component (C) is (B)/(C)=90/10 to 30/70, and the content of the component (B) is 1.6 to 14% by weight.

12. The method according to claim 11, comprising cleansing the skin.

* * * * *